US009526670B2

(12) United States Patent
Lee

(10) Patent No.: US 9,526,670 B2
(45) Date of Patent: *Dec. 27, 2016

(54) MASSAGE DEVICE HAVING SERIAL VIBRATORS

(71) Applicant: Wing Pow International Corp., Chatsworth, CA (US)

(72) Inventor: Calvin Spencer Lee, Northridge, CA (US)

(73) Assignee: Wing Pow International Corp., Chatsworth, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/983,406

(22) Filed: Dec. 29, 2015

(65) Prior Publication Data

US 2016/0128896 A1 May 12, 2016

Related U.S. Application Data

(63) Continuation of application No. 14/552,405, filed on Nov. 24, 2014, now Pat. No. 9,254,238, which is a (Continued)

(51) Int. Cl.
*A61F 5/00* (2006.01)
*A61H 19/00* (2006.01)
(Continued)

(52) U.S. Cl.
CPC .............. *A61H 19/44* (2013.01); *A61H 19/34* (2013.01); *A61H 23/00* (2013.01); *A61H 23/0263* (2013.01); *A61H 2201/5002* (2013.01)

(58) Field of Classification Search
CPC ........ A61H 19/00; A61H 19/34; A61H 19/40; A61H 19/44; A61H 23/00; A61H 23/0263
(Continued)

(56) References Cited

U.S. PATENT DOCUMENTS 3,417,743 A 12/1968 Carrera
4,515,167 A 5/1985 Hochman
(Continued)

FOREIGN PATENT DOCUMENTS

DE 33 16 100 A1 11/1984
DE 91 05 457 U1 2/1992
(Continued)

OTHER PUBLICATIONS

European Search Report dated Jan. 21, 2011 for European Patent Application No. EP 10 00 4179.
(Continued)

*Primary Examiner* — John Lacyk
(74) *Attorney, Agent, or Firm* — Laura M. Lloyd; Leech Tishman Fuscaldo & Lampl

(57) ABSTRACT

A mechanized dildo having a body with a plurality of vibrator assemblies, each vibrator assembly comprising a motor and a housing; a processor electrically coupled to each of the plurality of vibrator assemblies; a battery electrically coupled to the processor; at least one mode control switch electrically coupled to the processor; a phallic sleeve comprising an elastic material covers the plurality of vibrator assemblies; and a housing containing the processor, the battery and the at least one control switch; wherein the processor is configured to operate separate vibrator assemblies in different combination modes, such modes being selected using the at least one mode control switch.

17 Claims, 3 Drawing Sheets

Related U.S. Application Data continuation of application No. 14/163,004, filed on Jan. 24, 2014, now Pat. No. 8,915,835, which is a continuation of application No. 13/927,958, filed on Jun. 26, 2013, now Pat. No. 8,672,832, which is a continuation of application No. 12/574,630, filed on Oct. 6, 2009, now Pat. No. 8,496,572.

(51) Int. Cl.
*A61H 23/02* (2006.01)
*A61H 23/00* (2006.01)

(58) Field of Classification Search
USPC ........... 600/38–41; 601/46, 83–84, 101–103, 601/112–114, 117–118, 121
See application file for complete search history.

(56) References Cited

U.S. PATENT DOCUMENTS

| | | | |
|---|---|---|---|
| 4,779,615 | A | 10/1988 | Frazier |
| 4,909,263 | A | 3/1990 | Norris |
| 5,516,396 | A | 5/1996 | Maurer et al. |
| 5,561,879 | A | 10/1996 | Everall |
| 5,573,499 | A | 11/1996 | McAllister |
| 5,601,529 | A | 2/1997 | Wollman |
| 5,941,834 | A | 8/1999 | Skladnev |
| 6,063,022 | A | 5/2000 | Ben-Haim |
| 6,175,981 | B1 | 1/2001 | Lizama et al. |
| 6,350,230 | B1 | 2/2002 | Kontos |
| 6,378,150 | B1 | 4/2002 | Minegishi et al. |
| 6,647,572 | B2 | 11/2003 | Lee |
| 6,648,840 | B2 | 11/2003 | Cutler et al. |
| 6,741,895 | B1 | 5/2004 | Gafni et al. |
| 6,902,525 | B1 | 6/2005 | Jewell |
| 6,976,970 | B2 | 12/2005 | Siddhartha |
| 7,104,950 | B2 | 9/2006 | Levy |
| 7,438,681 | B2 | 10/2008 | Kobashikawa et al. |
| 7,503,892 | B2 | 3/2009 | Squicciarini |
| 7,527,589 | B2 | 5/2009 | Squicciarini |
| 7,608,037 | B2 | 10/2009 | Levy |
| 8,052,593 | B2 | 11/2011 | Jahns et al. |
| 8,496,572 | B2 | 7/2013 | Lee |
| 8,672,832 | B2 | 3/2014 | Lee |
| 8,915,835 | B2 | 12/2014 | Lee |
| 9,254,238 | B2 * | 2/2016 | Lee ........................ A61H 19/44 |
| 2003/0036678 | A1 | 2/2003 | Abbassi |
| 2003/0083590 | A1 | 5/2003 | Hochman et al. |
| 2004/0186344 | A1 | 9/2004 | Jannuzzi |
| 2005/0012406 | A1 | 1/2005 | Moret |
| 2005/0070827 | A1 | 3/2005 | Lee |
| 2005/0113636 | A1 | 5/2005 | Tucker |
| 2005/0113724 | A1 | 5/2005 | Wriggle |
| 2005/0159685 | A1 | 7/2005 | Klein et al. |
| 2006/0094992 | A1 | 5/2006 | Imboden et al. |
| 2006/0143092 | A1 | 6/2006 | Gardos et al. |
| 2007/0179414 | A1 | 8/2007 | Imboden et al. |
| 2008/0009775 | A1 | 1/2008 | Murison |
| 2008/0082028 | A1 | 4/2008 | Blevins |
| 2008/0119767 | A1 | 5/2008 | Berry et al. |
| 2008/0139980 | A1 | 6/2008 | Fladl et al. |
| 2008/0208083 | A1 | 8/2008 | Lin et al. |
| 2009/0093673 | A1 | 4/2009 | Lee |
| 2009/0093856 | A1 | 4/2009 | Attila et al. |
| 2009/0112055 | A1 | 4/2009 | Hyde et al. |
| 2009/0171144 | A1 | 7/2009 | Squicciarini |

FOREIGN PATENT DOCUMENTS

| | | |
|---|---|---|
| DE | 20 2008 011 722 U1 | 11/2008 |
| WO | 2009012172 A2 | 1/2009 |

OTHER PUBLICATIONS

Lee, Calvin Spencer, Office Action issued in related U.S. Appl. No. 12/574,630, filed Oct. 6, 2009, United States Patent Office, Dec. 13, 2012, 15 pages.
Lee, Calvin Spencer, Office Action issued in related U.S. Appl. No. 13/927,958, filed Jun. 26, 2013, United States Patent Office, Aug. 19, 2013, 19 pages.
Lee, Calvin Spencer, Office Action issued in parent U.S. Appl. No. 14/163,004, filed Jan. 24, 2014, United States Patent Office, May 8, 2014, 19 pages.
Lee, Calvin Spencer, Office Action issued in parent U.S. Appl. No. 14/552,405, filed Nov. 24, 2014, United States Patent Office, Jun. 5, 2015, 16 pages.

* cited by examiner

MASSAGE DEVICE HAVING SERIAL VIBRATORS

CROSS-REFERENCE TO RELATED APPLICATIONS

The present application is a continuation of U.S. patent application Ser. No. 14/552,405, filed on Nov. 24, 2014, which is a continuation of U.S. patent application Ser. No. 14/163,004, filed on Jan. 24, 2014, now U.S. Pat. No. 8,915,835 issued on Dec. 23, 2014, which is a continuation of U.S. patent application Ser. No. 13/927,958, filed on Jun. 26, 2013, now U.S. Pat. No. 8,672,832 issued on Mar. 18, 2014, which is a Continuation of U.S. patent application Ser. No. 12/574,630, filed on Oct. 6, 2009, now U.S. Pat. No. 8,496,572 issued on Jul. 30, 2013, the contents of which are incorporated in this disclosure by reference in their entirety.

BACKGROUND OF THE INVENTION

The present invention relates to sexual stimulation devices, and more particularly to a mechanized dildo.

Sexual stimulation devices of the prior art include dildos that have vibratory elements such as disclosed in U.S. Pat. No. 5,573,499, the entire contents of which are hereby incorporated herein by reference. However, it is believed that none of the devices of the prior art have proven entirely satisfactory, for a variety of reasons.

Thus there is a need for a sexual stimulation device in the form of a dildo that provides an improved form of stimulation and enhanced versatility as compared with existing devices.

BRIEF SUMMARY OF THE INVENTION

The present invention meets this need by providing a mechanized dildo that, according to an embodiment, features a body having a plurality of vibrator assemblies. Each vibrator assembly has a motor and a housing. A processor is electrically coupled to each of the plurality of vibrator assemblies. A battery and at least one mode control switch are electrically coupled to the processor. A phallic sleeve comprising an elastic material covers the plurality of vibrator assemblies. A housing contains the processor, the battery and the at least one control switch. The processor is configured to operate separate vibrator assemblies in different combination modes, such modes being selected using the at least one mode control switch. The mechanized dildo can have at least two vibrator assemblies. Optionally, the mechanized dildo has between two and seven vibrator assemblies.

In an embodiment of the present invention, each vibrator assembly housing has an enclosure having a projection; and a cap having a recess. The projection of one vibrator assembly fits into the recess of the adjacent vibrator assembly such that the vibrator assemblies are held in place against each other. Each projection and recess may be rounded, thereby allowing for rotation of each vibrator assembly relative to the any adjacent vibrator assemblies. The mechanized dildo may have a plurality of indicator lights for showing which combination was selected with the at least one mode control switch.

In another embodiment of the present invention, the mechanized dildo also has an arm transversely attached to the body, the arm comprising at least one arm vibrator assembly. The sleeve is configured to also cover the at least one arm vibrator assembly. Optionally, the at least one arm vibrator assembly is separately controllable from the body vibrator assemblies. The arm may have a plurality of arm vibrator assemblies. Optionally, the mechanized dildo has an arm mode control switch electrically coupled to the processor; and the processor is configured to operate the at least one arm vibrator assembly in different modes, such modes being selected using the arm mode control switch. The dildo may also have at least one arm mode indicator light for showing which mode was selected with the at least one arm mode control switch.

A mechanized dildo according to an additional embodiment of the present invention has a body with a plurality of vibrator assemblies, each vibrator assembly comprising a motor and a housing. A processor is electrically coupled to each of the plurality of vibrator assemblies. A battery is electrically coupled to the processor. At least one mode control switch is electrically coupled to the processor. An arm is transversely attached to the body, the arm having at least one arm vibrator assembly. An arm mode control switch is electrically coupled to the processor. A housing contains the processor, the battery, the at least one control switch and the arm mode control switch. A phallic sleeve having an elastic material is configured to cover the plurality of vibrator assemblies and the arm vibrator assembly. The processor is configured to operate the plurality of vibrator assemblies and the at least one arm vibrator assembly in different modes, such modes being selected using the at least one mode control switch and the arm mode control switch. In an embodiment, the mechanized dildo has at least five vibrator assemblies and a plurality of indicator lights for showing which modes were selected using the at least one mode control switch and the arm mode control switch.

BRIEF DESCRIPTION OF THE DRAWINGS

These and other features, aspects and advantages of the present invention will become better understood with regard to the following description, appended claims and accompanying figures where:

DETAILED DESCRIPTION

Figure 1:
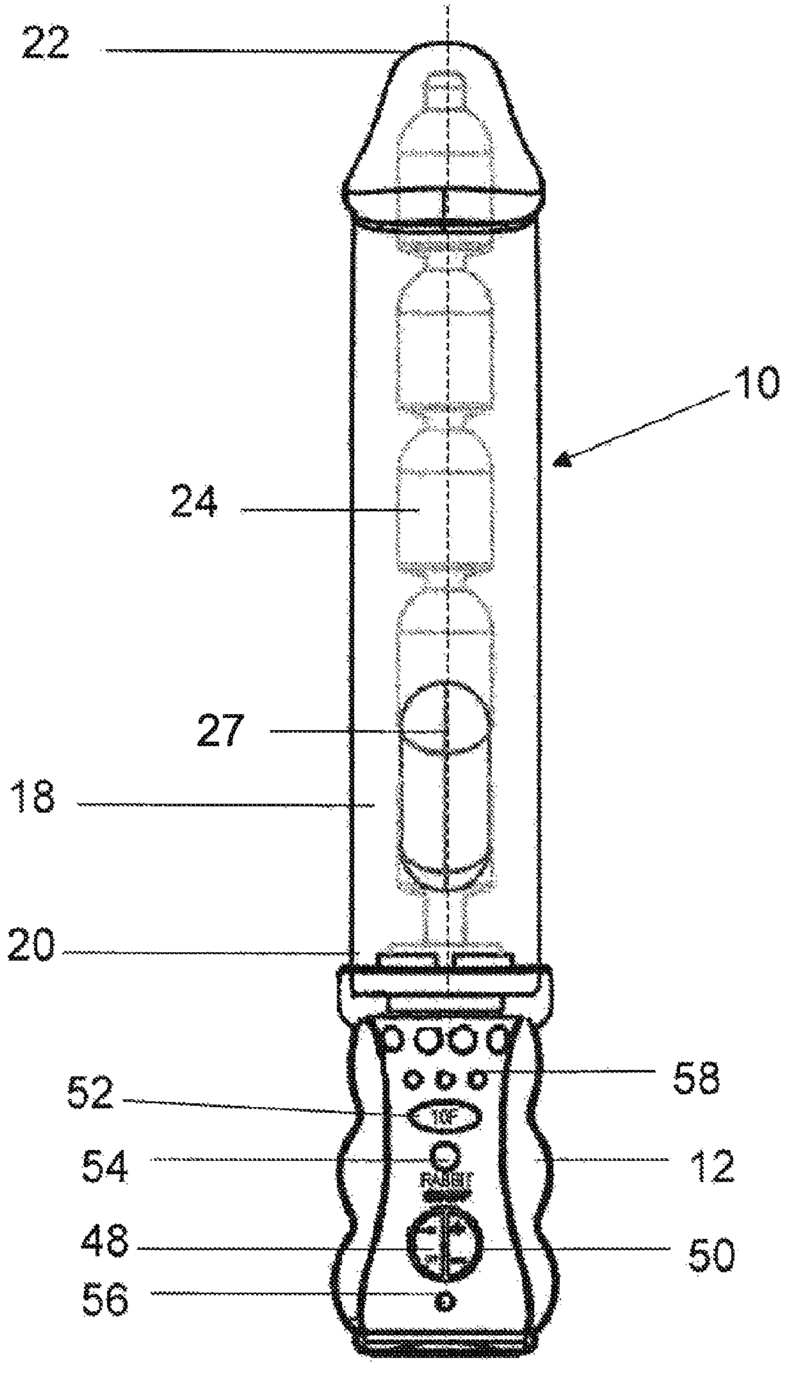
FIG. 1 is a perspective view of a mechanized dildo according to the present invention shown with a transparent sleeve so that the internal structure is visible.

The present invention is directed to a mechanized dildo that is particularly effective in stimulating female genitalia. With reference to FIGS. 1 to 4 of the drawings, a mechanized dildo 10 includes a base 12, a body 14 coupled to the base 12 and an arm 16 extending transversely from the body 14. The body and the arm are covered with a sleeve 18. The sleeve 18 is preferably made of an elastic material.

In a preferred embodiment of the present invention, the body 14 is configured for insertion into a human vagina and the arm 16 is configured for optimum stimulation of the human clitoris. However, as will be understood by those of skill in the art, the body 14 and the arm 16 can be configured for insertion into other orifices and for stimulation of other body parts.

The body 14 has a proximal end 20, a distal end 22 and extends along a longitudinal axis. The proximal end 20 is attached to the base 12. The body 14 has a plurality of separate vibrator assemblies 24. Each of the separate vibrator assemblies 24 is electrically connected to a controller 26 housed in the base 12. In an embodiment of the present invention, the body 14 has at least two separately controllable vibrator assemblies 24. In additional embodiments of the present invention, the body has at least 3, 4 or 5 separately controllable vibrator assemblies 24.

Each of the vibrator assemblies 24, and the arm vibrator assembly 27, preferably include a housing 28. In an embodiment, the housing 28 has an upper enclosure 30 and a lower cap 32. A motor 34 is positioned inside of the housing 28. The motor 34 rotates an eccentric weight member 36 in a conventional manner as further described below. Preferably, the lower cap 32 has an orifice to facilitate electrical connection of the motor 34 to the controller 26. Preferably, the housing is configured so that the vibrator assemblies can be positioned closely adjacent to each other.

In an embodiment of the present invention, the upper enclosure 30 has a projection 38 and the lower cap 32 has a recess 40. When the mechanized dildo is assembled the vibrator assemblies are stacked on top of each other with the projection 38 of one vibrating assembly placed in the recess 40 of the next vibrating assembly. All of the vibrating assemblies are held in place against each other, such as by the sleeve. In a preferred embodiment, the projections 38 and the corresponding recesses 40 are rounded, and preferably substantially hemispherical, thereby allowing for rotation of one vibrator assembly relative to another to allow the dildo 10 to be bendable.

Figure 2:
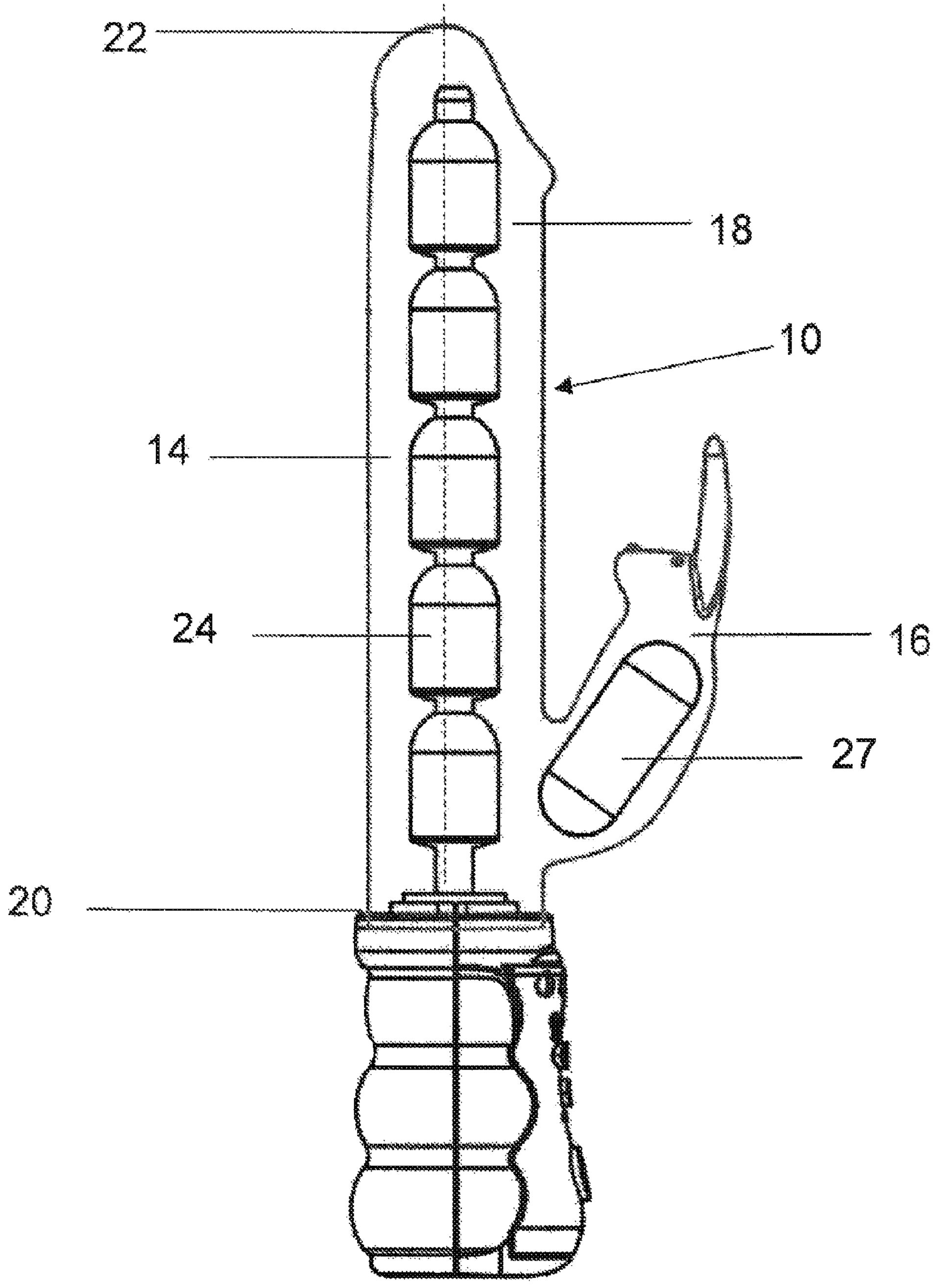
FIG. 2 is a perspective view of the mechanized dildo of FIG. 1 rotated 90 degrees around a longitudinal axis.
Figure 3:
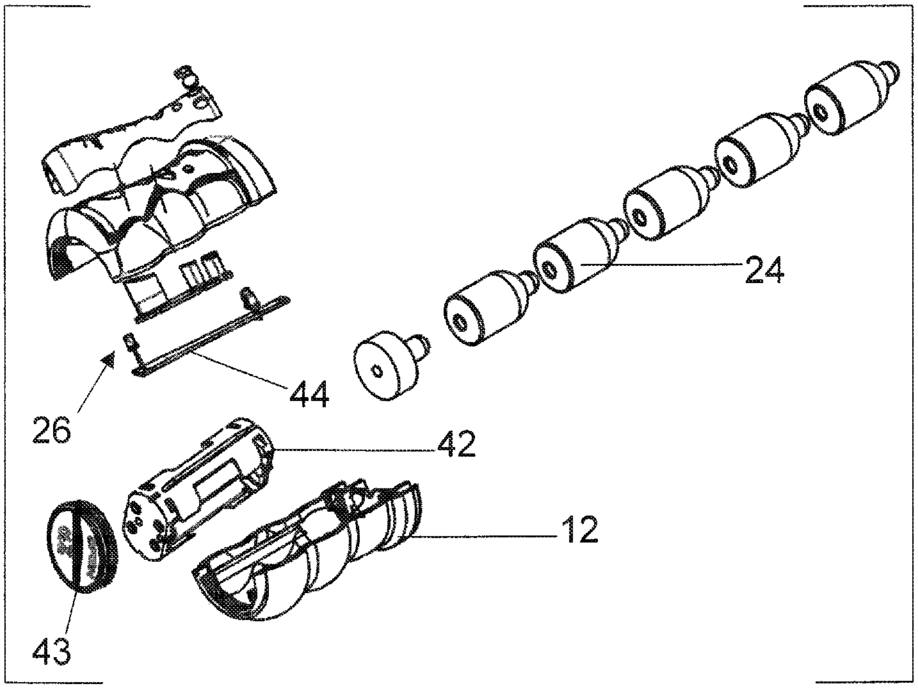
FIG. 3 is a perspective exploded view of the base and body of the mechanized dildo of FIG. 1 with the cover removed.
Figure 4:
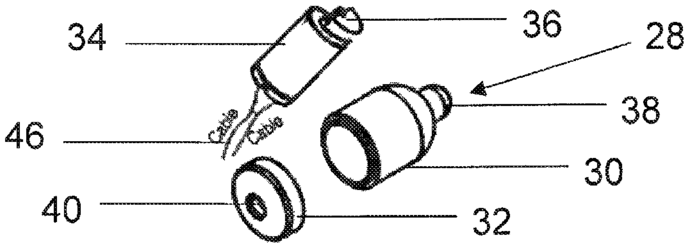
FIG. 4 is an exploded view of a vibrator assembly usable in the mechanized dildo of FIG. 1.

Preferably, the vibrator assemblies are arranged along the longitudinal axis as shown in FIGS. 1 to 3. In additional embodiments, the vibrator assemblies can be arranged with different orientations to each other and to the longitudinal axis.

In a preferred embodiment of the present invention, the arm 16 has at least one separately controllable arm vibrator assembly 27. However, in additional embodiments, the arm may be configured without a vibrator assembly or with a plurality of vibrator assemblies.

Preferably, the sleeve 18 has a nominal diameter of from approximately 1.2 inches (30 mm) to approximately 2.0 inches (50 mm), and a nominal length of from approximately 5 inches (127 mm) to approximately 9 inches (228 mm). Other dimensions are possible, depending on user preference. The arm is formed as a lateral extension of the phallic sleeve in a shape and dimension preferably facilitating contact with the clitoris of a user of the dildo.

The base 12 serves as a handle of the dildo 10 and encloses the controller 26 and a battery pack 42 which is retained in the base 12 by a removable cap 43. The controller 26 has a circuit board 44, there being appropriate wiring or other conductors, such as wires 46 between the battery pack 42, the circuit board 44, the vibrator assemblies 24 and the arm vibrator assembly 27.

In the configuration shown in FIGS. 1 to 4, the controller has a power switch actuator 48 for the vibrator assemblies 24, a mode switch actuator 50 for the vibrator assemblies 24, and a power switch actuator 52 for the arm vibrator assembly 27, and a mode switch actuator 54 for the arm vibrator assembly 27. Each actuator protrudes from the base for operation by a user. Each actuator has an associated switch (not shown) on the circuit board. A power indicator light 56 is visible through the base 12. Other indicator lights 58 extend through the base 12 to show which operation modes have been selected by the user. The mode switch actuator 50 for the vibrator assemblies sequentially selects a plurality of vibration combinations.

In an embodiment of the present invention, the body contains five separately controllable vibrator assemblies and 10 different modes of controlling the vibrator assemblies. The user selects from the different modes using the mode switch actuator 50. Examples of the 10 different modes are shown in the chart below. The status of each of the five vibrator assemblies at each step in each mode is shown with a "1" to designate that the particular vibrator assembly is on or a "0" to designate that the particular vibrator assembly is off. The examples are for illustration purposes only, and the modes may have many different combinations of vibrator assemblies depending on the number of vibrator assemblies and user preferences.

| Mode | Pattern of Vibrator Assembly Control |
|---|---|
| 1 | 10000-01000-00100-00010-00001 and then circulation |
| 2 | 00001-00010-00100-01000-10000 and then circulation |
| 3 | 11000-01100-00110-00011-11111 and then circulation |
| 4 | 10101-01010-10101-01010-10101 and then circulation |
| 5 | 10000-11000-10100-10010-10001 and then circulation |
| 6 | 10000-11010-10101-11010-10101 and then circulation |
| 7 | 00100-01010-10001-11000-11011 and then circulation |
| 8 | 10010-01001-11000-00110-00011 and then circulation |
| 9 | 11000-01100-00110-00011-11111 and then circulation |
| 10 | 11100-01110-00111-11000-00110-00011-10000-01000-00100-00010-00001 and then circulation |

In additional embodiments, when the arm vibrator assembly has been activated, the different modes may be controlled to vary in coordination with the vibrator assemblies in the body.

Suitable materials for the vibrator housing, the control housing and the switch actuators include ABS. Suitable materials for the battery module include polypropylene; and suitable materials for the phallic sleeve include elastic plastic materials such as TPE. A suitable battery compartment contains is configured to contain four type AAA batteries.

Although the present invention has been discussed in considerable detail with reference to certain preferred embodiments, other embodiments are possible. Therefore, the scope of the appended claims should not be limited to the description of preferred embodiments contained in this disclosure. All references cited herein are incorporated by reference in their entirety.

All features disclosed in the specification, including the claims, abstract and drawings, can be combined in any combination except combinations where at least some of such features and/or steps are mutually exclusive. Each feature disclosed in the specification, including the claims, abstract, and drawings can be replaced by alternative features serving the same, equivalent or similar purpose, unless expressly stated otherwise. Thus, unless expressly stated otherwise, each feature disclosed is a one example only of a generic series of equivalent or similar features.

Any element in a claim that does not explicitly state "means" for performing a specified function or "step" for performing a specified function, should not be interpreted as a "means" or "step" clause as specified in 35 U.S.C. §112.

What is claimed is:

1. A mechanized dildo comprising:

a) a base;

b) a body extending from the base, the body having a proximal section and a distal section, wherein the proximal section is proximate to the base, and the distal section is distal to the base;

c) a plurality of vibrator assemblies along the body, including a first vibrator assembly at the proximal section of the body and a second vibrator assembly at the distal section of the body, each vibrator assembly comprising a motor and a housing, and each vibrator assembly being separately controllable;

d) a controller electrically coupled to each of the plurality of vibrator assemblies for controlling the vibration of each vibrator assembly separately;

e) a power source electrically coupled to the controller;

f) at least one mode selection switch electrically coupled to the controller;

g) an arm transversely attached to the body, the arm comprising at least one arm vibrator assembly;

h) an arm mode selection switch electrically coupled to the controller; and i) a phallic sleeve comprising an elastic material which covers the plurality of vibrator assemblies and the arm vibrator assembly;

wherein the base contains the controller, the power source, the at least one mode selection switch, and the arm mode selection switch, and the controller is configured to operate separate ones of the plurality of vibrator assemblies and the at least one arm vibrator assembly in different modes, such modes being selected using the at least one mode selection switch and the arm mode selection switch.

2. The mechanized dildo of claim 1, wherein the plurality of vibrator assemblies comprises at least five vibrator assemblies.

3. The mechanized dildo of claim 1, further comprising a plurality of indicator lights for showing which modes were selected using the at least one mode selection switch and the arm mode selection switch.

4. The mechanized dildo of claim 1, further comprising a third vibrator assembly between the first and second vibrator assemblies.

5. A mechanized dildo comprising:

a) a base;

b) a body extending from the base, the body having a proximal section and a distal section, wherein the proximal section is proximate to the base, and the distal section is distal to the base;

c) a plurality of vibrator assemblies along the body, including a first vibrator assembly at the proximal section of the body and a second vibrator assembly at the distal section of the body, each vibrator assembly comprising a motor and a housing and each vibrator assembly being separately controllable and spaced apart from the other vibrator assemblies;

d) a controller electrically coupled to each of the plurality of vibrator assemblies for controlling the vibration of each vibrator assembly separately; and e) a power source electrically coupled to the controller;

wherein the base contains the controller and the power source, and the controller is configured to operate separate ones of the plurality of vibrator assemblies in different modes.

6. The mechanized dildo of claim 5, wherein the base comprises a handle.

7. The mechanized dildo of claim 6, further comprising a phallic sleeve, the phallic sleeve comprising an elastic material and covering the plurality of vibrator assemblies.

8. The mechanized dildo of claim 5, further comprising a third vibrator assembly between the first and second vibrator assemblies.

9. A mechanized dildo comprising:

a) a body having a proximal section and a distal section;

b) a plurality of spaced apart vibrator assemblies along the body, including a first vibrator assembly at the proximal section of the body and a second vibrator assembly at the distal section of the body, each vibrator assembly comprising a motor and a housing and being separately controllable;

c) a controller electrically coupled to each of the plurality of vibrator assemblies and adapted for electrically actuating the vibration of each vibrator assembly; and d) a power source electrically coupled to the controller;

wherein the controller is configured to operate separate ones of the plurality of vibrator assemblies in different modes.

10. The mechanized dildo of claim 9, further comprising a third vibrator assembly between the first and second vibrator assemblies.

11. The mechanized dildo of claim 9, wherein the controller has at least one of the following modes:

a) the controller is configured to sequentially actuate the vibrator assemblies, wherein only one vibrator assembly vibrates at a time;

b) during a first interval of time, the controller is configured to actuate and vibrate two of the vibrator assemblies along the body while another vibrator assembly along the body is not actuated and does not vibrate, and in another interval of time, the controller is configured to actuate and vibrate all of the vibrator assemblies along the body simultaneously;

c) wherein the plurality of vibrator assemblies comprises at least four vibrator assemblies, and during a first interval of time, the controller is configured to actuate and vibrate three of the vibrator assemblies along the body simultaneously while another vibrator assembly along the body is not actuated and does not vibrate, and in another interval of time two of the vibrator assemblies are actuated and vibrate simultaneously while another vibrator assembly along the body is not actuated and does not vibrate;

d) during a first interval of time, the controller is configured to actuate and vibrate one vibrator assembly along the body while another vibrator assembly along the body is not actuated and does not vibrate, and in a second interval of time two of the vibrator assemblies are actuated and vibrate simultaneously while another vibrator assembly along the body is not actuated and does not vibrate, and in a third interval of time two of the vibrator assemblies are actuated and vibrate simultaneously while another vibrator assembly along the body is not actuated and does not vibrate;

e) wherein the plurality of vibrator assemblies comprises at least four vibrator assemblies, and during a first interval of time, the controller is configured to actuate and vibrate one vibrator assembly along the body while another vibrator assembly along the body is not actuated and does not vibrate, and in another interval of time three of the vibrator assemblies are actuated and vibrate simultaneously while another vibrator assembly along the body is not actuated and does not vibrate, wherein the intervals of time alternate;

f) wherein the plurality of vibrator assemblies comprises at least four vibrator assemblies, and during a first interval of time, the controller is configured to actuate and vibrate one vibrator assembly along the body while another vibrator assembly along the body is not actuated and does not vibrate, in a second interval of time two of the vibrator assemblies are actuated and vibrate simultaneously while another vibrator assembly along the body is not actuated and does not vibrate, and in a third interval of time four of the vibrator assemblies are actuated and vibrate simultaneously while another vibrator assembly along the body is not actuated and does not vibrate;

g) the controller is configured to actuate and vibrate two of the vibrator assemblies along the body simultaneously while another vibrator assembly along the body is not actuated and does not vibrate; and h) wherein the plurality of vibrator assemblies comprises at least four vibrator assemblies, and during a first interval of time, the controller is configured to actuate and vibrate three of the vibrator assemblies along the body simultaneously while another vibrator assembly along the body is not actuated and does not vibrate, in a second interval of time two of the vibrator assemblies are actuated and vibrate simultaneously while another vibrator assembly along the body is not actuated and does not vibrate, and in a third interval of time one vibrator assembly is actuated and vibrates while another vibrator assembly along the body is not actuated and does not vibrate.

12. The mechanized dildo of claim 9, wherein the plurality of vibrator assemblies comprises between three and seven vibrator assemblies.

13. The mechanized dildo of claim 7, further comprising an arm transversely attached to the body, the arm comprising at least one arm vibrator assembly, and wherein the sleeve is configured to also cover the at least one arm vibrator assembly.

14. The mechanized dildo of claim 13, wherein the arm comprises a plurality of arm vibrator assemblies.

15. The mechanized dildo of claim 13, wherein the at least one arm vibrator assembly is separately controllable from the body vibrator assemblies.

16. The mechanized dildo of claim 7, further comprising:

a) an arm transversely attached to the body, the arm comprising at least one arm vibrator assembly; and b) an arm mode selection switch electrically coupled to the controller;

wherein the sleeve is configured to also cover the at least one arm vibrator assembly, and the controller is configured to operate the at least one arm vibrator assembly in different modes, such modes being selected using the arm mode selection switch.

17. The mechanized dildo of claim 16, further comprising at least one arm mode indicator light for showing which mode was selected with the at least one arm mode selection switch.

* * * * *